United States Patent [19]
Watatani et al.

[11] Patent Number: 5,858,337
[45] Date of Patent: Jan. 12, 1999

[54] INTERMEDIATE TREATMENT COMPOSITION FOR PERMANENT WAVE

[75] Inventors: Kazuyo Watatani, Chiba; Hiroyuki Koga, Funabashi; Naohisa Kure, Tokyo, all of Japan

[73] Assignee: Kao Corporation, Tokyo, Japan

[21] Appl. No.: 943,206

[22] Filed: Oct. 3, 1997

Related U.S. Application Data

[63] Continuation of Ser. No. 424,525, filed as PCT/JP93/01393 Sep. 29, 1993, abandoned.

[30] Foreign Application Priority Data

Apr. 16, 1992 [JP] Japan ..................................... 4-96488

[51] Int. Cl.⁶ ................ A61K 7/09; A61K 7/06
[52] U.S. Cl. ................... 424/70.2; 705/70.5; 705/70.51; 832/210
[58] Field of Search ................. 424/70.2, 70.5, 424/70.51; 132/210

[56] References Cited

U.S. PATENT DOCUMENTS

| | | | |
|---|---|---|---|
| 3,864,476 | 2/1975 | Altieri | 424/71 |
| 3,958,581 | 5/1976 | Abegg | 132/7 |
| 4,331,167 | 5/1982 | Wajaroff | 132/7 |
| 4,895,722 | 1/1990 | Ake | 424/71 |
| 5,350,512 | 9/1994 | Savaides | 424/71 |
| 5,441,729 | 8/1995 | Salce | 424/70.2 |

FOREIGN PATENT DOCUMENTS 3-153621 7/1991 Japan.

OTHER PUBLICATIONS

Manufacturing Chemist, vol. 59, No. 4, pp. 42–44, "Permanent Waving" Apr., 1988.

*Primary Examiner*—Sally Gardner-Lane
*Attorney, Agent, or Firm*—Oblon, Spivak, McClelland, Maier & Neustadt, P.C.

[57] ABSTRACT

An intermediate treatment composition for permanent wave, comprising at least one carbonate and/or at least one hydrogencarbonate.

When the hair is treated with the intermediate treatment composition for permanent wave between treatments with the first and second compositions, mixed disulfides formed in the hair by the treatment with the first composition can be cleaved. Therefore, the wave-forming rate can be enhanced, and damage to the hair can also be prevented.

13 Claims, No Drawings

INTERMEDIATE TREATMENT COMPOSITION FOR PERMANENT WAVE

This application is a continuation of application Ser. No. 08/424,525, filed on May 30, 1995, abandoned, which was filed as International Application No. PCT/JP93/01393, on Sep. 29, 1993.

TECHNICAL FIELD

The present invention relates to an intermediate treatment composition for permanent wave, and more particularly to an intermediate treatment composition for permanent wave, which serves to cleave mixed disulfides formed in the hair by a treatment with a first-package permanent wave composition which is within a range of from acidity to weak alkalinity, thereby enhancing permanent wave-forming ability, and can prevent damage to the hair to be caused by permanent waving. BACKGROUND ART Permanent waving for giving the hair the desired waves is a method in which S—S bonds in the hair are subjected to reductive chain cleavage with a first-package permanent wave composition (hereinafter referred to as "the first composition") comprising, as a principal component, a reducing agent such as thioglycolic acid or cysteine, and then to oxidative chain closure with a second-package permanent wave composition (hereinafter referred to as "the second composition") comprising, as a principal component, an oxidizing agent such as a bromate, perborate or aqueous hydrogen peroxide.

However, the reduction of the hair by the first composition is generally conducted under alkaline conditions of pH 8–10. Therefore, such phenomena that proteins and/or lipids in the hair are dissolved out, the strength of the hair is lowered and the feel of the hair to the touch is deteriorated have been caused. Such hair has involved a problem that when the hair is groomed to fix in a desired hair style, smooth brushing or combing can not be performed so that a brush or comb may be caught by the hair, which causes separation of hair cuticle, split hairs and broken hairs, resulting in damage to the hair.

Therefore, various intermediate treatment compositions for permanent wave have heretofore been provided with a view toward preventing such damage to the hair by the permanent waving to improve a feel of the hair to the touch, and enhancing wave-forming ability. For example, the damage to the hair is prevented by adding a hydrolyzate of keratin as described in Japanese Patent Application Laid-Open No. 246509/1987, or by adding a hydrolyzate of a protein as described in GB 2 160 419 A. Further, in U.S. Pat. No. 4,494,557, magnesium sulfate and a mixture of a hydrolyzate of a protein, oily substance, surfactant, inorganic salt and the like are used to enhance wave-forming ability and hence to keep waves longer.

However, the conventional intermediate treatment compositions for permanent wave can only suppress a feeling of damage to the hair and improve the feel of the hair to the touch, but neither essentially improve the damage to the hair, nor have satisfactory wave-forming ability.

On the other hand, low-damage permanent waving in which the pH of a first-package permanent wave composition has been adjusted within a range of from acidity to weak alkalinity for the purpose of suppressing the swelling of the hair and preventing proteins and amino acids from dissolving out has been conducted. However, in such a pH, mixed disulfides which are combination products of a cysteine residue in the hair with a mercapto compound are formed during the reductive cleavage of S—S bonds by a reducing agent such as thioglycolic acid, cysteine or glyceryl monothioglycolate, so that the subsequent oxidation by the second composition becomes incomplete. Therefore, such a treatment has involved a drawback that waving efficiency in the permanent waving becomes low, and the damage to the hair is also unavoidable.

It is thus an object of the present invention to provide an intermediate treatment composition for permanent wave, which can provide excellent wave-forming ability even in permanent waving making use of the first composition whose pH is within a range of from acidity to weak alkalinity, and prevent damage to the hair.

In view of the foregoing circumstances, the present inventors have carried out an extensive investigation. As a result, it has been found that carbonates and hydrogen-carbonates are useful for the cleavage of mixed disulfides, and the use of an intermediate treatment composition for permanent wave with these salts incorporated therein permits both enhancement of wave-forming rate for the hair and prevention of damage to the hair, leading to completion of the present invention.

DISCLOSURE OF THE INVENTION

The present invention is related to an intermediate treatment composition for permanent wave, comprising at least one carbonate and/or at least one hydrogencarbonate.

The present invention is also related to a permanent-waving process, which comprises treating the hair with a first-package permanent wave composition, with an intermediate treatment composition for permanent wave including at least one carbonate and/or at least one hydrogencarbonate and then with a second-package permanent wave composition.

The intermediate treatment composition for permanent wave according to the present invention serves to cleave mixed disulfides formed in the hair by a treatment with a first-package permanent wave composition which is within a range of from acidity to weak alkalinity, thereby enhancing permanent wave-forming ability, and can prevent the hair from being damaged by permanent waving.

BEST MODE FOR CARRYING OUT THE INVENTION

Examples of the carbonate useful in the practice of the present invention include sodium carbonate, potassium carbonate, ammonium carbonate, sodium potassium carbonate, lithium carbonate, cesium carbonate, calcium carbonate, magnesium carbonate, etc. Examples of the hydrogen-carbonate include sodium hydrogencarbonate, potassium hydrogencarbonate, ammonium hydrogencarbonate, magnesium potassium hydrogencarbonate, lithium hydrogencarbonate, ammonium hydrogencarbonate carbamate, etc. Of these, sodium carbonate, potassium carbonate, ammonium carbonate, sodium potassium carbonate, sodium hydrogencarbonate, potassium hydrogencarbonate, ammonium hydrogencarbonate and magnesium potassium hydrogencarbonate are particularly preferred.

These carbonates and hydrogencarbonates may be used either singly or in any combination thereof, and may preferably be incorporated in a total proportion of 0.5–10 wt. % (hereinafter indicated merely by "%"), particularly 1–5% into the intermediate treatment composition for permanent wave.

The intermediate treatment composition for permanent wave according to the present invention can effectively cleave the mixed disulfides at a pH within a range of from weak acidity to alkalinity. It is also preferable to adjust the pH of the composition to 6–10, particularly 8–10. If the pH is lower than 6, sufficient effects can not be achieved. On the other hand, any pH levels exceeding 10 are not very preferred from the viewpoint of irritation. Examples of pH adjustors used for adjusting the composition to such a pH include weak acids such as citric acid, succinic acid, acetic acid, lactic acid, tartaric acid, glycine and aspartic acid, or salts thereof, alkalis such as sodium hydroxide, potassium hydroxide, ammonia, monoethanolamine, diethanolamine and triethanolamine, basic amino acids such as lysine and arginine, etc.

In the intermediate treatment compositions for permanent wave according to the present invention, optional ingredients which are used routinely as needed, for example, surfactants, solvents, oily substances, moisturizers, colorants, emulsifiers, perfume bases, etc. may be suitably incorporated in addition to the above-described essential ingredients. Besides, a cationic polymer described in Japanese Patent Application Laid-Open No. 92812/1981, amphoteric polymer or silicone such as dimethyl polysiloxane, methylphenyl polysiloxane, cyclic silicone, polyether-modified silicone and amino-modified silicone may also be incorporated to enhance the hair-protective effect.

The intermediate treatment compositions for permanent wave according to the present invention can be formulated by dissolving the essential and optional ingredients in water or an aqueous solvent to form a solution, milky lotion, aerosol or the like.

The thus-obtained intermediate treatment composition for permanent wave according to the present inventions is used by applying or spraying it to the hair between treatments with the first and second compositions in the usual permanent waving process. It is particularly preferable to treat the hair with the first composition which is within a range of from acidity to alkalinity, then with the intermediate treatment composition of this invention, and finally with the second composition.

As the first-package permanent wave composition which is within a range of from acidity to weak alkalinity, may preferably be used a common composition comprising thioglycolic acid, its salt or its ester derivative such as glyceryl monothioglycolate, L-cysteine, N-acetyl-cysteine, thiolactic acid, or the like and adjusted to pH 4–8. As the second-package permanent wave composition, may preferably be used a composition comprising, as a principal component, an oxidizing agent such as a bromate, perborate, hydrogen peroxide of iodine.

EXAMPLES

The present invention will hereinafter be described in more detail by the following examples. However, it should be borne in mind that this invention is not limited to and by these examples.

Examples 1–3, Comparative Examples 1–2

In a permanent waving treatment making use of the following first- and second-package cold wave compositions, the hair was treated with their corresponding intermediate treatment compositions for permanent wave (Examples 1–3, Comparative Example 1) shown in Table 1 between treatments with the first and second compositions. At this time, degree of permanent wave was evaluated by determining degree of waving and diameter of curl. The results are shown in Table 2.

Chemicals Used (1) First-package cold wave composition:

Ammonium thioglycolate 7.0 (%)

Water, phosphoric acid 93.0 (adjusted to pH 6.5 with phosphoric acid)

(2) Second-package cold wave composition:

Sodium bromate 5.0 (%)

Water 95.0

Besides, the hair was treated with a first-package cold wave composition having a composition described below and the second composition of the above composition without using any intermediate treatment composition for permanent wave. At this time, degree of permanent wave was also evaluated by determining degree of waving and diameter of curl. The results are shown as Comparative Example 2 in Table 2.

Chemicals Used (1) First-package cold wave composition:

Ammonium thioglycolate 7.0 (%)

Ammonium hydrogencarbonate 4.0

Water, phosphoric acid 89.0 (adjusted to pH 6.5 with phosphoric acid)

TABLE 1

| | (%) | | | |
| --- | --- | --- | --- | --- |
| | Example | | | Comp. Ex. |
| | 1 | 2 | 3 | 1 |
| Ammonium hydrogen-carbonate | 4.0 | | | |
| Sodium carbonate | | 4.0 | | |
| Sodium hydrogen-carbonate | | | 4.0 | |
| Ammonium chloride | | | | 4.0 |
| Deionized water | Balance | Balance | Balance | Balance |
| pH* | 8.0 | 8.0 | 8.0 | 8.0 |

*Adjusted with phosphoric acid for Examples 1–3, and with sodium hydroxide for Comparative Example 1.

Evaluation Methods (1) Degree of waving:

Ten Japanese hairs of 15 cm in length, which had been subjected to bleaching and permanent waving each once in accordance with the respective methods known per se in the art, were bundled to wind the resulting bundle around a glass tube (10 mm in diameter). The hair-wound glass tube was immersed for 20 minutes at 30° C. in the first composition. The glass tube was immersed for 10 minutes in the intermediate treatment composition (Examples 1–3, Comparative Example 1), then for 10 minutes in the second composition. After the thus-treated hair bundle was thoroughly washed with water, it was taken out of the glass tube. As a result, the hair bundle was curled in the form of a coil. At this time, the length of a coil of the hair bundle was measured to determine a degree of waving in accordance with the following equation.

Besides, with respect to Comparative Example 2, a hair-wound glass tube was immersed for 30 minutes at 30° C. in the first composition and then for 10 minutes directly in the second composition without conducting any intermediate treatment. A degree of waving was then determined in the same manner as described above.

$$\text{Degree of waving} = \frac{X - Y}{X} \times 100$$

X: The whole length of the hair bundle (15 cm)
Y: The length of the coil of the hair bundle (cm).
(2) Diameter of curl:
An inner diameter of the coil of the hair bundle, which had been obtained in the test (1), was measured, and termed "diameter of curl (mm)".

Results

TABLE 2

|  | Degree of waving (%) | Diameter of curl (mm) |
| --- | --- | --- |
| Ex. 1 | 40.0 | 19 |
| Ex. 2 | 41.0 | 20 |
| Ex. 3 | 41.5 | 20 |
| Comp. Ex. 1 | 21.5 | 23 |
| Comp. Ex. 2 | 38.0 | 26 |

It is understood from the results of Table 2 that when the intermediate treatment compositions for permanent wave according to the present invention is used, the degree of permanent wave becomes good.

Example 4:

Using the same intermediate treatment composition for permanent wave as used in Example 3, permanent waving was conducted in the same manner as in Examples 1–3 and Comparative Example 1. At this time, changes in modulus of elasticity of the hair after the treatments with the first composition, the intermediate treatment composition for permanent wave and the second composition were determined. The results are shown in Table 3. Incidentally, the numerical values in Table 3 are numerical values calculated regarding the modulus of elasticity of the hair before the first treatment as 100.

TABLE 3

| Before treatment | After treatment with first composition | After application of intermediate treatment composition for permanent wave | After treatment with second composition |
| --- | --- | --- | --- |
| 100 | 51 | 78 | 100 |

It is understood from the results of Table 3 that the use of the intermediate treatment composition for permanent wave according to the present invention does not cause the reduction of modulus of elasticity of the hair.

Example 5:

The hair was treated with an intermediate treatment composition for permanent wave of a composition described below between treatments with the same first and second compositions as used in Example 1. As a result, it was found that degree of permanent wave is good as with Examples 1–3, and damage to the hair is also prevented.

| (Composition) | (%) |
| --- | --- |
| Ammonium hydrogencarbonate | 4.0 |
| Propylene glycol | 2.0 |
| Stearyltrimethylammonium chloride (28%) | 1.0 |
| Polyoxyethylene lauryl ether (23 E.O.) | 0.5 |
| Perfume base | 0.05 |
| Amino-modified silicone* | 1.0 |
| Aqueous ammonia (28%) | Proper amount** |
| Deionized water | Balance |
|  | 100.0 |

*Toray Silicone SM8702C (Toray Industries, Inc.)
**Amount to pH 8.0.

INDUSTRIAL APPLICABILITY

When the hair is treated with the intermediate treatment composition for permanent wave according to the present invention between treatments with the first and second compositions, mixed disulfides formed in the hair by the treatment with the first composition can be cleaved. Therefore, the wave-forming rate can be enhanced, and damage to the hair can also be prevented.

We claim:
1. A permanent waving process which comprises:
   a) treating hair with a first-package permanent wave composition having a pH of 4–8 to affect cleavage of S—S bonds in said hair; then,
   b) treating said hair with an intermediate treatment composition for permanent wave, consisting essentially of at least one carbonate or at least one hydrogen carbonate or both to cleave mixed disulfides formed in said hair by treatment with said first-packaged permanent wave composition; and then,
   c) treating said hair with a second-package wave composition.
2. The permanent-waving process of claim 1, wherein the intermediate treatment composition for permanent wave comprises at least one carbonate or at least one hydrogencarbonate compound or both in an amount of about 0.5 to 10% by weight based on the total weight of the composition.
3. The permanent-waving process of claim 2, wherein the amount used of the at least one carbonate or hydrogen carbonate or both is about 1 to 5% by weight.
4. The permanent-waving process of claim 1, wherein the intermediate treatment composition has a pH of about 6 to 10.
5. The permanent-waving process of claim 1, wherein said at least one carbonate is selected from the group consisting of sodium carbonate, potassium carbonate, ammonium carbonate, sodium potassium carbonate, lithium carbonate, cesium carbonate, calcium carbonate and magnesium carbonate.
6. The permanent-waving process of claim 1, wherein said at least one hydrogencarbonate is selected from the group consisting of sodium hydrogencarbonate, potassium hydrogencarbonate, ammonium hydrogencarbonate, magnesium potassium carbonate, lithium hydrogencarbonate, and ammonium hydrogencarbonate carbamate.
7. The permanent-waving process of claim 4, wherein the intermediate treatment composition has a pH of about 8 to 10.
8. The permanent-waving process of claim 1, wherein said intermediate treatment composition further comprises a cationic polymer, an amphoteric polymer or a silicone polymer.

9. The permanent-waving process of claim 8, wherein said silicone polymer is selected from the group consisting of dimethyl polysiloxane, methylphenyl polysiloxane, cyclic silicone, polyether-modified silicone and amino-modified silicone.

10. The permanent-waving process of claim 1, wherein said intermediate treatment composition further comprises an optional ingredient selected from the group consisting of surfactants, solvents, oily substances, moisturizers, colorants, emulsifiers and perfume bases.

11. The permanent waving process of claim 1, wherein said second-package permanent wave composition effects oxidative chain closure.

12. The permanent waving process of claim 1, wherein said second-package permanent wave composition comprises an oxidizing agent selected from the group consisting of bromate, perborate, hydrogen peroxide, iodine and a mixture thereof.

13. The permanent waving process of claim 11, wherein said first-package permanent wave composition comprises an element selected from the group consisting of thioglycolic acid, glyceryl monothioglycolate, L-cysteine, N-acetyl-cysteine, thiolactic acid and a mixture thereof.

* * * * *

UNITED STATES PATENT AND TRADEMARK OFFICE
CERTIFICATE OF CORRECTION

PATENT NO. : 5,858,337
DATED : January 12, 1999
INVENTOR(S) : Kazuyo Watatani, et. al.

It is certified that error appears in the above-identified patent and that said Letters Patent is hereby corrected as shown below:

On the title page, Item [30], the Foreign Application Priority Data, should be deleted. Priority is not being claimed.

Column 8, Line 6 "claim 11," should read --claim 1,--

Signed and Sealed this

Twenty-first Day of September, 1999

Attest:

Q. TODD DICKINSON

*Attesting Officer*   Acting Commissioner of Patents and Trademarks